(12) United States Patent
Derer

(10) Patent No.: US 10,546,098 B2
(45) Date of Patent: Jan. 28, 2020

(54) CLAIM REIMBURSEMENT VALUATION AND REMITTANCE VALIDATION

(71) Applicant: Passport Health Communications, Inc., Franklin, TN (US)

(72) Inventor: Richard Frank Derer, Westmont, IL (US)

(73) Assignee: Passport Health Communications, Inc., Franklin, TN (US)

( * ) Notice: Subject to any disclaimer, the term of this patent is extended or adjusted under 35 U.S.C. 154(b) by 908 days.

(21) Appl. No.: 14/577,562

(22) Filed: Dec. 19, 2014

(65) Prior Publication Data
US 2016/0180034 A1 Jun. 23, 2016

(51) Int. Cl.
*G06F 19/00* (2018.01)
*G06Q 40/08* (2012.01)

(52) U.S. Cl.
CPC .......... *G06F 19/328* (2013.01); *G06Q 40/08* (2013.01)

(58) Field of Classification Search
CPC ....... G06Q 40/00; G06Q 40/08; G06F 19/328
See application file for complete search history.

(56) References Cited

U.S. PATENT DOCUMENTS

| | | | | |
|---|---|---|---|---|
| 7,904,317 B1* | 3/2011 | Lesswing | ............... | G06Q 10/10 705/2 |
| 2003/0018496 A1* | 1/2003 | Hambright | ............. | G06Q 30/04 705/2 |
| 2006/0106653 A1* | 5/2006 | Lis | ......................... | G06Q 20/10 705/4 |
| 2010/0211413 A1* | 8/2010 | Tholl | .................... | G06Q 10/00 705/4 |
| 2010/0257126 A1* | 10/2010 | Tolan | .................... | G06Q 10/04 705/500 |

* cited by examiner

*Primary Examiner* — Sheetal R Paulson
(74) *Attorney, Agent, or Firm* — Merchant & Gould

(57) ABSTRACT

A claim valuation engine is provided. The claim valuation engine enables a healthcare provider to accurately value an expected reimbursement of a claim from a payer based on a contract between the healthcare provider and the payer. Contract terms, code sets, fee schedules, and other valuation data is input into the engine. The engine receives a claim from a healthcare provider information system, locates a contract applicable for valuing the claim, correlates the claim attributes with the contract terms according to a hierarchy, and determines an expected reimbursement for each claim attribute or group of attributes. The claim valuation engine is further operable to determine contractual allowances, determine under and overpayments by validating remittances, and to simulate valuation of a contract by valuing a claim based on multiple sets of contract terms. The engine is further operable to generate output reports and post results to the healthcare provider information system.

7 Claims, 5 Drawing Sheets

CLAIM REIMBURSEMENT VALUATION AND REMITTANCE VALIDATION

BACKGROUND

Healthcare providers, such as hospitals, doctors, dentists, etc., maintain what is known as a charge master, which is a schedule of list prices for each chargeable procedure, item, or service provided by the healthcare provider. When a patient receives healthcare services from a healthcare provider, payments for the services are typically paid by a third party payer, such as a social insurance program, a social welfare program, or a private insurance company. Most often, the healthcare provider has a contract with the third party payer that defines how the provider will be reimbursed by the payer, which may be a negotiated discount off the charge master prices, a set amount, or other negotiated amount. For example, if a given payer is a private insurance company, the healthcare provider may be paid on a basis of per-diems or fee-for-service schedules. A given healthcare provider may have contracts with a large number of third party payers, wherein each payer may pay different amounts for a procedure or service based on the contract it has with the provider. As can be appreciated, calculating an expected reimbursement from a payer can be complicated and error-prone. It is with respect to these and other considerations that the present invention has been made.

SUMMARY

Various aspects of a claim reimbursement valuation and remittance validation system enable a healthcare provider to accurately value an expected reimbursement of a claim from a payer based on a contract between the healthcare provider and the payer. Contract terms, code sets, fee schedules, and other valuation data is input into a claim valuation engine. The claim valuation engine receives a claim from a healthcare provider information system, locates a contract applicable for valuing the claim, and loads the claim attributes and contract terms into a table. The claim valuation engine correlates the claim attributes with the contract terms according to a hierarchy, and determines an expected reimbursement for each claim attribute or group of attributes. The claim valuation engine is further operable to determine contractual allowances, determine under and over payments by validating remittances, and to simulate valuation of a contract by valuing a claim based on multiple sets of contract terms. The claim valuation engine is further operable to generate output reports and post results to the healthcare provider information system.

BRIEF DESCRIPTION OF DRAWINGS

Further features, aspects, and advantages of the invention represented by the embodiments described present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

A claim reimbursement valuation and remittance validation system and methods are described herein and illustrated in the accompanying figures. According to an aspect, the claim reimbursement valuation and remittance validation system enables a healthcare provider to accurately value a claim for reimbursement from a third party payer according to contract terms agreed upon between the healthcare provider and the third party payer. Additionally, the claim reimbursement valuation and remittance validation system enables a healthcare provider to compare actual reimbursements to expected reimbursements, and identify payment variances. According to another aspect, the claim reimbursement valuation and remittance validation system enables a healthcare provider to value a claim with multiple sets of contract terms. Accordingly, the healthcare provider can model various "what if" scenarios, for example, to calculate and compare expected reimbursements by two third party payers.

Figure 1:
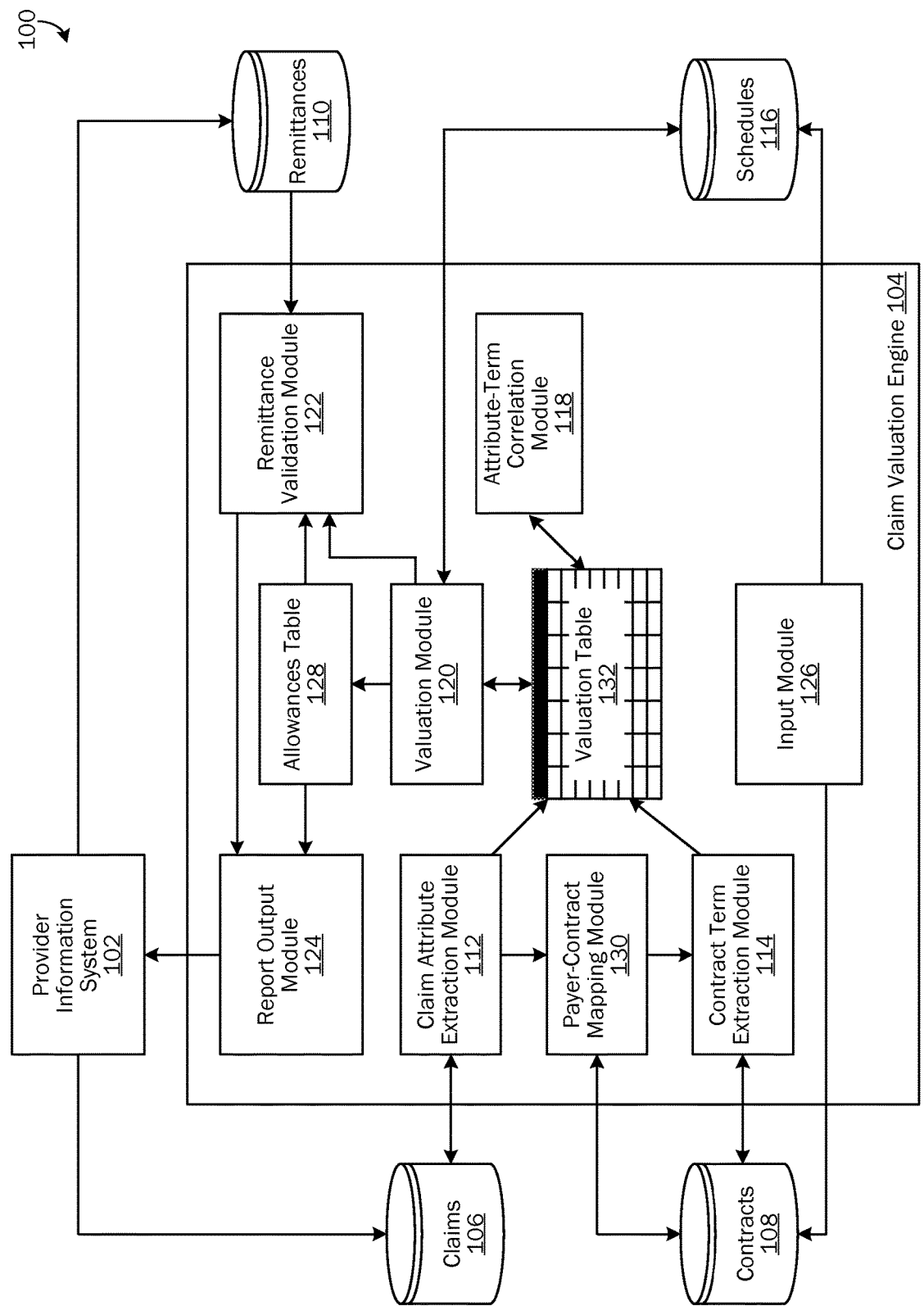
FIG. 1 is a simplified block diagram illustrating an example of a claim reimbursement valuation and remittance validation system.

Referring now to FIG. 1, a simplified block diagram of an example claim reimbursement valuation and remittance validation system 100 is illustrated. As should be appreciated, implementation of the system 100 may operate as a single computing device or as a distributed system, where each component operates on remote computing devices and is accessed via a suitable network. The one or more computing devices may be one of various types of computing devices (e.g., a desktop computer, a tablet computing device, a mobile communication device, a laptop computer, a laptop/tablet hybrid computing device, or other types of computing devices) for executing applications for performing a variety of tasks, for example, the claim valuation engine 104.

As illustrated, the claim reimbursement valuation and remittance validation system 100 includes a claim valuation engine 104. According to an aspect, the claim valuation engine 104 is operable to receive contract terms, build a contract based on the contract terms, access a claim, determine a payer or payers responsible for reimbursement of the claim, access a payer contract, read the claim attributes and contract terms into a table 132, correlate the claim attributes with the contract terms according to a hierarchy, and value an expected claim reimbursement and contractual allowance. According to an aspect, the results are posted to a host system, such as a healthcare provider information system 102. Utilization of the claim valuation engine 104 increases efficiency of the computing device, and thus increases the speed of output and the ability to process large volumes of data (e.g., claims).

The claim valuation engine 104 comprises an input module 126 operable to receive input of contract information into the claim reimbursement valuation and remittance validation system 100, and to store the contract information in a contracts repository 108. According to an aspect, a user interface is provided for enabling an information worker, such as a contract specialist or payment analyst, to enter contract information, such as a contract's name, rate set, reimbursement terms, and criteria used to match contract terms to claim attributes, into the system 100, and to build a contract from the entered contract information. For example, a contract specialist or payment analyst is enabled to interpret a contract to determine what terms to define in the system 100 for valuation of claims. Contract terms are stored in rate sets and are given effective date ranges, which are used to determine which terms apply when valuing a claim. According to an aspect, various contract terms can be input and defined in the system 100, such as: a priority level, which is used to create a valuation hierarchy; a category, which is used as a description of the term; and a valuation type, which defines what type of calculation to perform (e.g., percentage, flat rate, etc.) to value a given contract term. According to an aspect, additional contract terms are input or selected when applicable, such as: a limit type, which is used to modify a calculation by setting a maximum; a limit amount, which is required for certain limit types; a secondary type, which works in conjunction with the primary limit to provide an alternate calculation when the primary limit is reached; fee schedules, which are used to retrieve a reimbursement value; DRG code sets and base rates, which are used to retrieve relative weights and adjustment rates; coinsurance percentage, if applicable, to modify by a primary calculation; an add-on, which is used to instruct the claim valuation engine 104 to value with the given term if criteria is met and then continue to look for additional matching terms; and a carve-out, which behaves like an add-on and also reduces total charges by an amount of the reimbursement value. The input module 126 is further operable to receive input of or selection of a payer to which to link the contract.

The input module 126 is operable to receive, import, or copy various code sets, fee schedules, groupers, and base rates (herein collectively referred to as schedules), and store the schedules in a schedules repository 116. According to an aspect, the schedules are stored in tables. For example, the schedules repository 116 stores one or more of the following types of information: fee schedules (schedule with CPT codes and dollar amount), ASC (Ambulatory Surgical Center—schedule with CPT codes and grouper), OST (schedule with CPT codes and tiers, but not grouper), CRI (schedule with CPT codes, used as criteria), CRT (schedule with CPT codes and tiers used as criteria), DRG (Diagnostic Related Group—schedule with DRG codes and dollar amount, used as a fee schedule), PHY (Physician schedule, but not standard Medicare), PX (ICD9 procedure codes, used as criteria), REV (Revenue codes, used as criteria), DRC (DRG codes used as criteria), ASL (schedule with CPT codes, grouper, and a dollar cap), and various schedules and addenda used by Medicare.

According to an aspect, schedules are used to value claims depending on the valuation type. As described above, the valuation type defines what type of valuation or calculation to perform to value a term. For example, valuation types comprise, but are not limited to, APC (Ambulatory Payment Classification—Medicare Outpatient), APG (Ambulatory Payment Grouper—Medicaid Outpatient), APL (Ambulatory Procedure List), Combined Carveout, DRG (Diagnostic Related Group—Medicare Inpatient), DRG Case, EAPGI/EAPGO (Enhanced Ambulatory Patient Grouping—Inpatient/Outpatient, F2360, Flat Rate or Case Rate, Percent, Per Unit, Per Visit, Individual Charge Percent, and Schedule. For example, a DRG valuation type gets its reimbursement from a DRG code set. A DRG code table (i.e. DRG schedule) comprising DRG code criteria is entered, copied, or imported and stored. The claim valuation engine 104 matches the DRG of a claim with entries in the specified DRG schedule, and values a reimbursement amount based on weights entered in the table.

Referring still to FIG. 1, the claim valuation engine 104 comprises a claim attribute extraction module 112 operable to access a claim, read claim attributes from the claim, and load the claim attributes into a valuation table 132. The claim is provided by a healthcare provider information system 102, and according to an aspect, is stored in a claims repository 106 for access by the claim attribute extraction module 112. The claim is sent to the claim valuation engine 104 in a standardized format according to HIPAA (Health Insurance Portability and Accountability Act) requirements, for example, an EDI 837 transaction set. According to an aspect, claims are sent from the healthcare provider information system 102 one-by one. According to another aspect, claims are sent in a batch from the healthcare provider information system 102 for processing by the claim valuation engine 104.

The claim attribute extraction module 112 is operable to read a claim and identify a payer (e.g., a social insurance program, a social welfare program, or a private insurance company) based on information in the claim. According to an aspect, the claim attribute extraction module 112 is in communication with a payer-contract mapping module 130 with which the claim attribute extraction module 112 communicates the identified payer. The payer-contract mapping module 130 is operable to locate a contract linked to the identified payer and stored in the contracts repository 108. Once a contract is located, a contract term extraction module 114 is called to read the contract and load the contract terms into the valuation table 132.

The claim valuation engine 104 comprises an attribute-term correlation module 118 that is in communication with the valuation table 132 and operable to identify each claim attribute read from the claim, and correlate the claim attribute with a contract term read from the contract. According to an aspect, the correlation module 118 is further operable to logically group each claim attribute. For example, some procedures are priced within the context of other procedures, such as tiered Ambulatory Surgical Procedures (ASP), where the first procedure may price at 100% of the schedule amount, the second procedure may price at 50% of the schedule amount, etc. As described above, when contract information is input into the system 100, the information comprises a priority level used to create a valuation hierarchy. According to an aspect, the contract terms are matched according to the valuation hierarchy, where terms starting with Priority 1 are considered top priority and correlated first.

The claim valuation engine 104 comprises a valuation module 120. When a correlation is made by the attribute-term correlation module 118, a reimbursement is valued by the valuation module 120. If a correlation is not made, the attribute-term correlation module 118 reads the next hierarchical contract term for matching the claim attributes with the contract term's criteria. According to an aspect, the attribute-term correlation module 118 continues to look for correlations in hierarchical order, depending on how the contract is defined, either until it hits a full-claim term or until the last term in the hierarchy is correlated. For example, if the highest priority contract term in a given contract is to indicates to parse the claim for certain DRG codes according to a DRG schedule, and the claim includes an attribute with a DRG code that matches the criteria, a correlation is made, and the claim attribute is valued based on weights in the DRG schedule. The contract term is a full-claim term if it satisfies the valuing of the claim. Valued claim attributes for each contract term are written to an allowances table 128.

According to an aspect, the claim valuation engine 104 further comprises a report output module 124 operable to generate a valuation report comprising an expected reimbursement for claims as valued by the claim valuation engine 104, and post the valuation report to a host system, for example, a healthcare provider information system 102. According to an aspect, the valuation module 120 is further operable to calculate contractual allowances, that is, differences between charges and the valued claim reimbursements. Accordingly, the report output module 124 is further operable to generate an allowance report, and post the allowance report to the healthcare provider information system 102.

According to an aspect, the claim valuation engine 104 comprises an remittance validation module 122. The remittance validation module 122 is operable to receive a remittance item, match the remittance item with a claim and claim reimbursement value determined by the valuation module 120, and identify a variance between a remittance and a claim reimbursement value. A remittance item comprises information of a payment made in response to a claim for provision of healthcare services. According to an aspect, remittance items are stored in a remittance repository 110. The remittance validation module 122 is in communication with the report output module 124, which is further operable to generate a variance report comprising identified variances between remittances and claim reimbursement values, and post the variance report to the healthcare provider information system 102.

Figure 2:
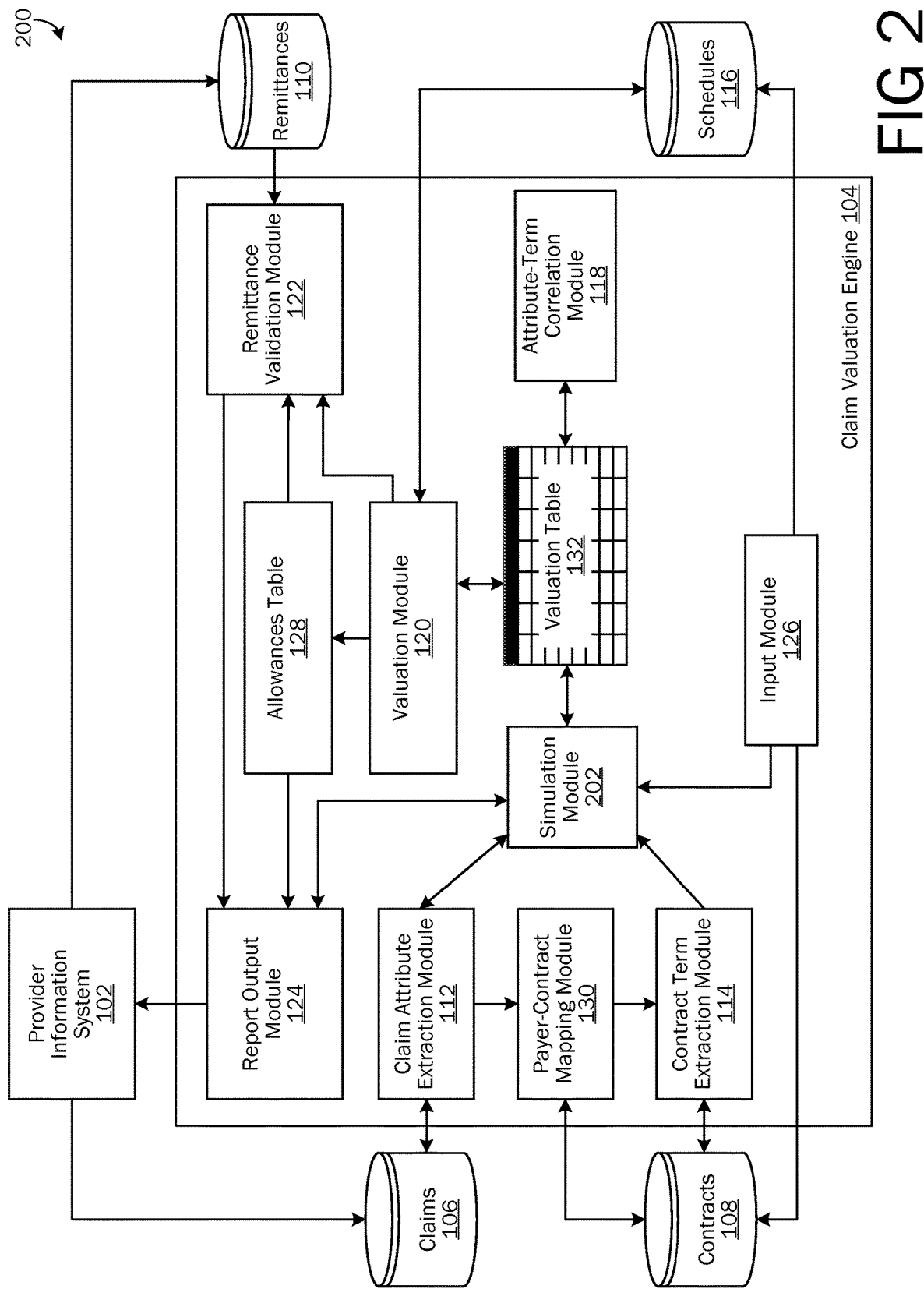
FIG. 2 is a simplified block diagram illustrating an example of a claim reimbursement valuation and remittance validation system comprising a simulation module.

With reference now to FIG. 2, a simplified block diagram of another example claim reimbursement valuation and remittance validation system 200 is illustrated. According to an aspect, the system 200 comprises the components of the system 100 illustrated in FIG. 1, and further comprises a simulation module 202 operable to value claim reimbursements with multiple sets of contract terms. For example, healthcare providers continually renegotiate their contracts with health-insurance companies (i.e., third party payers). When negotiating the terms of contracts with payers, it is desirable for the healthcare providers to maximize their reimbursements from insurance companies based on their case mix. The example claim reimbursement valuation and remittance validation system 200 enables a healthcare provider to take a current set of contract terms, select or generate a second set of proposed contract terms, and run one or more claims through both sets of terms to determine how the provider would fare under the current set verses the proposed set of contract terms. Accordingly, the system 200 allows a healthcare provider to help fashion a contract with a payer based on the types of claims that the provider typically submits.

According to an aspect, a set of contract terms comprises contract terms associated with a contract linked to a payer and stored in the contracts repository 108. According to another aspect, a set of contract terms comprises proposed contract terms that an information worker, such as a contract specialist or payment analyst, is enabled to input via the input module 126. The ability to value claims with multiple sets of contract terms can be very useful in performing 'what if' scenarios. The input module is further operable 126 to receive a selection of a single claim or a plurality of claims to value. According to an aspect, claims are selectable by admission date ranges and patient type: inpatient, outpatient or all patient types.

The simulation module 202 is operable to receive the selected or input contract terms and a selection of one or more claims, load the contract terms and claim attributes into the valuation table 132 for valuation by the valuation module 120. The claim valuation engine 104 of the example claim reimbursement valuation and remittance validation system 200 comprises a report output module 124 operable to generate a simulation report comprising claim reimbursement values for the one or more claims according to the multiple sets of contract terms. For example, a simulation report comprises results of values for a first contract vs a second contract such that values of a claim reimbursement can be compared side-by-side. According to an aspect, the simulation report comprises details of values of individual or grouped claim attributes such that the healthcare provider is enabled to compare for which procedures they will be reimbursed more based on the current contract terms versus proposed contract terms.

Figure 3:
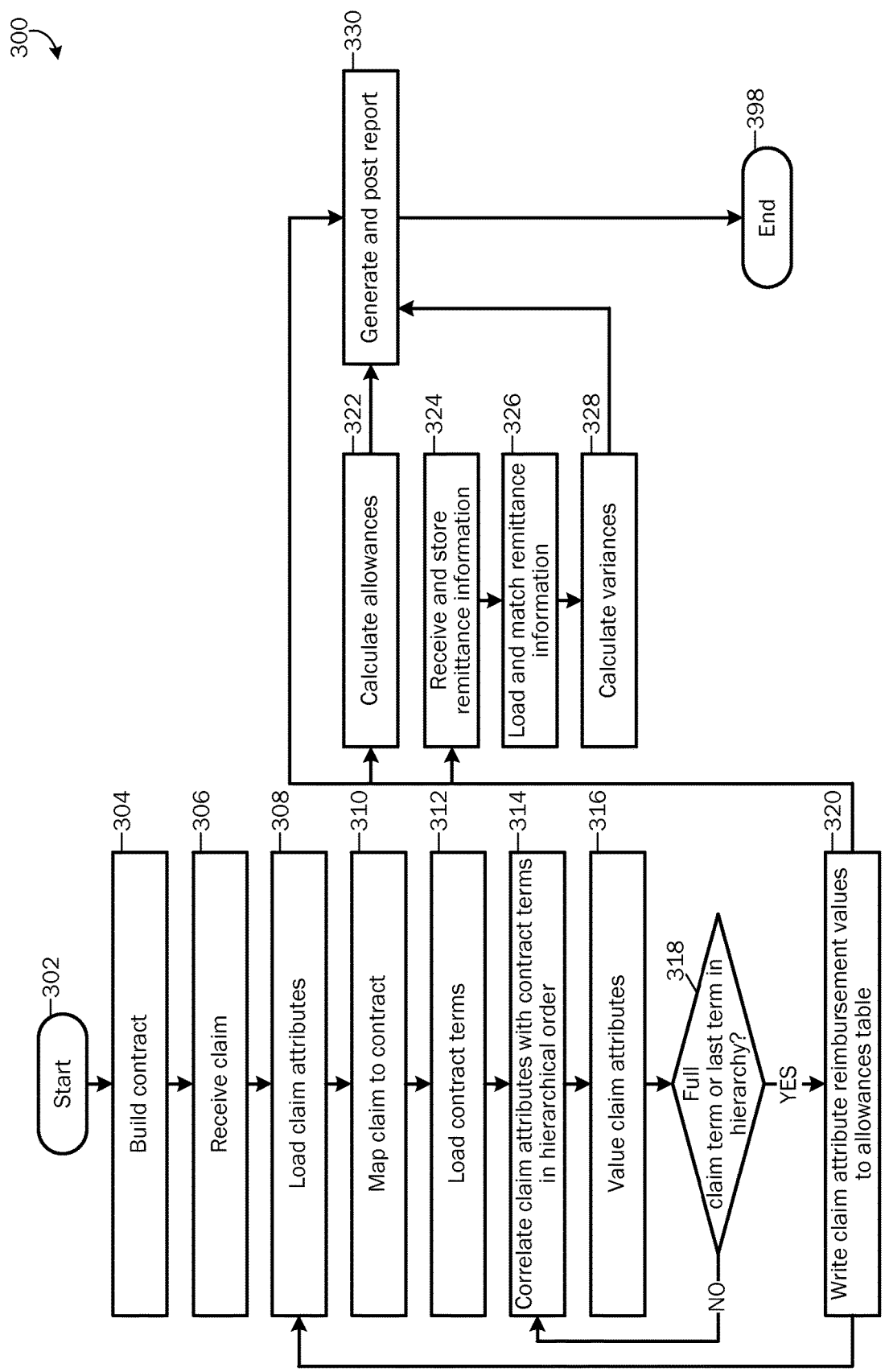
FIG. 3 is a flow chart of a method for valuing a claim reimbursement.

FIG. 3 is a flow chart of a method 300 for valuing a claim reimbursement. The method 300 starts at OPERATION 302, and proceeds to OPERATION 304, where a contract is built from contract information input via the input module 126 into the claim valuation engine 104, and stored in the contracts repository 108. According to an aspect, claim information comprises a contract's name, rate set, reimbursement terms, and criteria used to match contract terms to claim attributes. According to an aspect, during OPERATION 304, an appropriate payer is linked to the contract via input of a payer identifier and a plan code.

At OPERATION 306, one or a plurality of claims are received from a provider information system 102. According to an aspect, the one or more claims are sent in a standardized format according to HIPAA (Health Insurance Portability and Accountability Act) requirements, for example, an EDI 837 transaction set.

The method 300 proceeds to OPERATION 308, where claim attributes from a claim of the one or more received claims are loaded into a valuation table 132. A payer identifier specifying an appropriate payer of the claim is including in the claim attributes, which, at OPERATION 310, is utilized to map the claim to a contract stored in the contracts repository 108. According to an aspect, the claim attributes comprise service date information, which is utilized by the payer-contract mapping module 130 to ensure a correct version of a contract is mapped.

At OPERATION 312, the contract term extraction module 114 extracts the contract terms from the contract and loads the contract terms into the valuation table 132. At OPERATION 314, the valuation module 120 correlates the claim attributes with the contract terms. According to an aspect, the claim attributes are correlated in hierarchical order, where claim attributes with contract terms starting with Priority 1 are correlated first. When a correlation is made, a reimbursement is valued at OPERATION 316.

At DECISION OPERATION 318, a determination is made as to whether a contract term correlated at OPERATION 316 is a full-claim term or the last term in the hierarchy. If the contract term correlated at OPERATION 316 is not a full-claim term nor the last term in the hierarchy, the method returns to OPERATION 314, where a claim attribute or group of attributes is correlated with a next hierarchical contract term. If at DECISION OPERATION 318 a determination is made that a contract term correlated at OPERATION 316 satisfies the valuing of the claim, the method 300 proceeds to OPERATION 320, where the claim attribute reimbursement values are written to an allowances table 128. If there are additional claims to value, the method 300 returns to OPERATION 308.

According to an aspect, the method proceeds from OPERATION 320 to OPERATION 330, where the report output module 124 generates a report of the valued claims and posts the report to the healthcare provider information system 102. According to another aspect, the method 300 proceeds from OPERATION 320 to OPERATION 322, where allowances (difference between charge amounts and valued reimbursement amounts of claim attributes) are calculated. At OPERATION 330, an allowance report is generated and posted to the healthcare provider information system 102. According to another aspect, the method proceeds from OPERATION 320 to OPERATION 324, where remittance information is received from the healthcare provider information system 102 and stored in the remittances repository 110.

The method 300 proceeds from OPERATION 324 to OPERATION 326, where the remittance validation module 122 retrieves a remittance item from the remittance repository 110, and matches the remittance item with a claim and claim reimbursement value determined by the valuation module 120 at OPERATION 316. According to an aspect, the remittance item comprises information of a payment made in response to the claim for provision of healthcare services.

The method 300 proceeds to OPERATION 328, where the remittance validation module 122 identifies a variance between the remittance amount and the claim reimbursement value. According to an aspect, the remittance validation module 122 is operable to identify variances between remittance amounts and reimbursement values per claim attribute. At OPERATION 330, a variance report comprising identified variances between remittances and claim reimbursement values is generated and posted to the healthcare provider information system 102. The method 300 ends at OPERATION 398.

Figure 4:
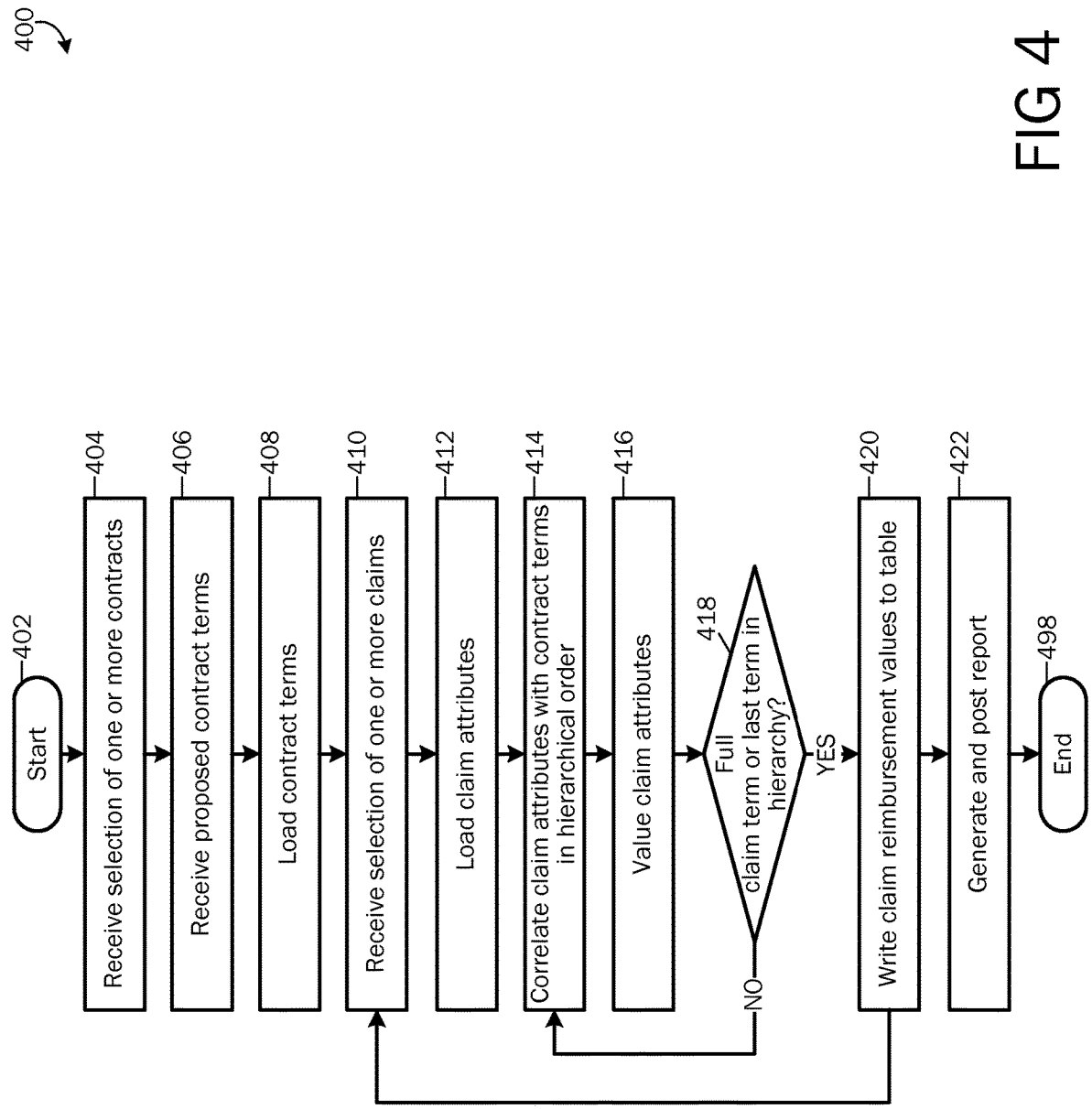
FIG. 4 is a flow chart of a method for simulating contract terms and valuing claim reimbursements.

FIG. 4 is a flow chart of a method 400 for valuing a claim reimbursement with multiple sets of contract terms, for example, to simulate valuation of a proposed contract. The method 400 starts at OPERATION 402, and proceeds to OPERATION 404, where an indication of a selection of one or more existing contracts stored in the contracts repository 108 is received. The method 400 proceeds to OPERATION 406, where proposed contract terms are input via the input module 126, for example, contract terms for a proposed contract for negotiations with a payer.

At OPERATION 408, the proposed contract terms are loaded into the valuation table 132 and the contract term extraction module 114 extracts the contract terms from the one or more selected (existing) contracts and loads the contract terms into the valuation table 132. The method 400 proceeds to OPERATION 410, where one or more claims stored in the claims repository 106 are selected for valuation per the multiple sets of contract terms. At OPERATION 412, the claims attributes of the one or more selected claims are extracted and loaded into the valuation table 132.

The method 400 proceeds to OPERATION 414, where the valuation module 120 correlates the claim attributes of a first claim with a first set of contract terms. According to an aspect, the claim attributes of a claim are correlated in hierarchical order, where claim attributes with contract terms starting with Priority 1 are correlated first. When a correlation is made, a reimbursement is valued at OPERATION 416.

At DECISION OPERATION 418, a determination is made as to whether a contract term correlated at OPERATION 416 is a full-claim term or the last term in the hierarchy. If the contract term correlated at OPERATION 416 is not a full-claim term nor the last term in the hierarchy, the method returns to OPERATION 414, where a claim attribute or group of attributes is correlated with a next hierarchical contract term. If at DECISION OPERATION 418 a determination is made that a contract term correlated at OPERATION 416 satisfies the valuing of the claim, the method 400 proceeds to OPERATION 420, where the claim attribute reimbursement values are written to an allowances table 128. Each claim is valued according to each set of contract terms. If there are additional claims to value, the method 400 returns to OPERATION 408.

The method proceeds from OPERATION 420 to OPERATION 422, where the report output module 124 generates a simulation report comprising claim reimbursement values for the one or more claims according to the multiple sets of contract terms, and posts the report to the healthcare provider information system 102. The method 400 ends at OPERATION 498.

Aspects of the present disclosure are implemented via local, remote, or a combination of local and remote computing and data storage systems. Such memory storage and processing units are implemented in a computing device, such as computing device 500. Any suitable combination of hardware, software, or firmware is used to implement the memory storage and processing unit. For example, the memory storage and processing unit is implemented with computing device 500 or any other computing devices 518, in combination with computing device 500, wherein functionality is brought together over a network in a distributed computing environment, for example, an intranet or the Internet, to perform the functions as described herein. Such systems, devices, and processors (as described herein) are examples and other systems, devices, and processors comprise the aforementioned memory storage and processing unit, consistent with embodiments of the invention.

Figure 5:
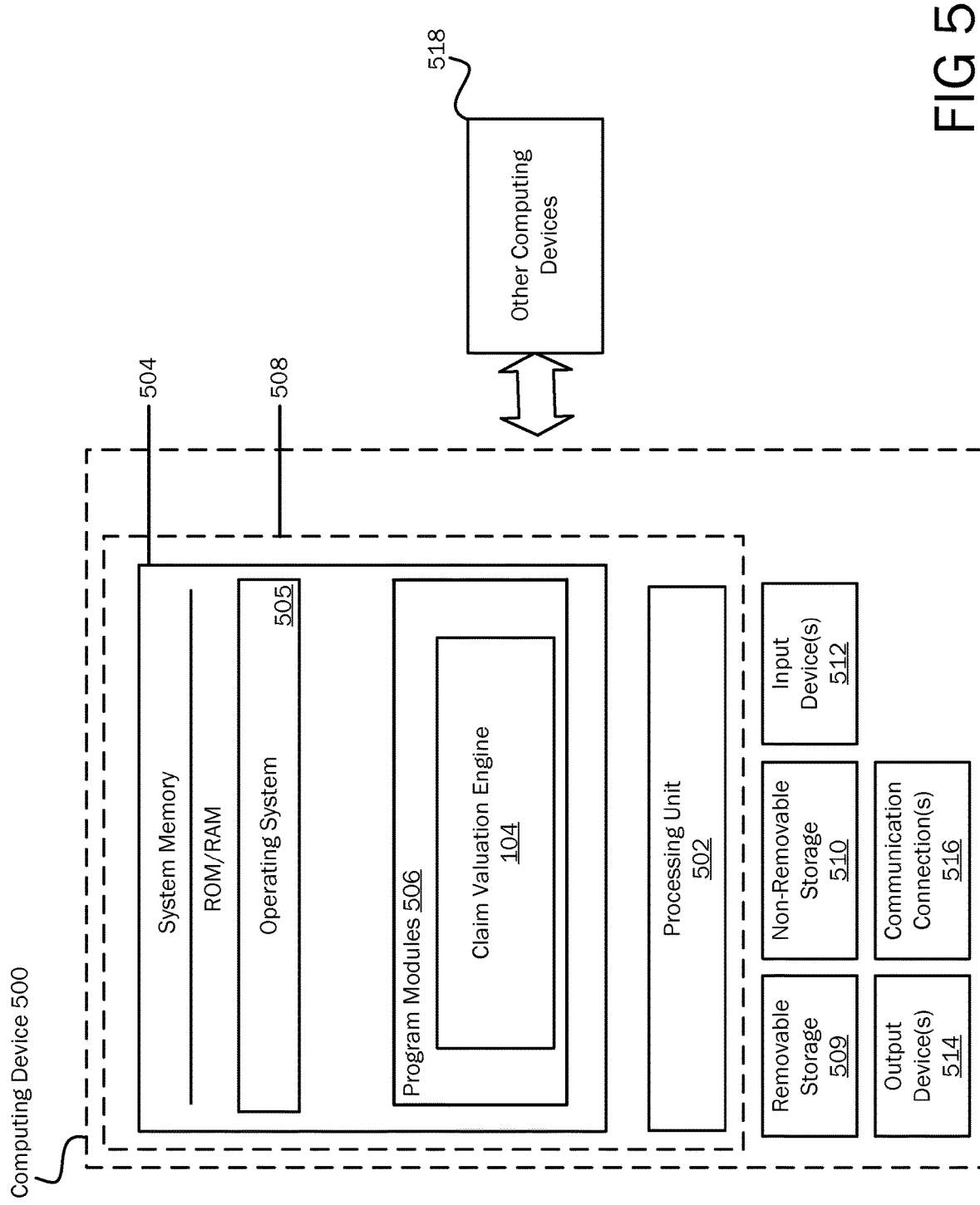
FIG. 5 is a simplified block diagram of a computing device with which aspects of the present disclosure may be practiced.

FIG. 5 illustrates one example of a computing device suitable to implement aspects of the present disclosure. The computing device 500 includes at least one processing unit 502 and a system memory 504. The system memory 504 comprises, but is not limited to, volatile (e.g. random access memory (RAM)), non-volatile (e.g. read-only memory (ROM)), flash memory, or any combination. System memory 504 includes operating system 505, one or more programming modules 506, and according to an aspect, includes the claim valuation engine 104, which when executed, performs functionalities as described herein. Operating system 505, for example, is suitable for controlling the operation of computing device 500. Furthermore, According to an aspect, features of the present disclosure are practiced in conjunction with a graphics library, other operating systems, or any other application program, and is not limited to any particular application or system. This basic configuration is illustrated by those components within a dashed line 508. According to an aspect, computing device 500 includes one or more input device(s) 512 (keyboard, mouse, pen, touch input device, etc.) and one or more output device(s) 514 (e.g., display, speakers, a printer, etc.).

According to an aspect, the computing device 500 includes additional data storage devices 509/510 (removable and/or non-removable) such as, for example, magnetic disks, optical disks, or tape. According to an aspect, computing device 500 comprises a communication connection 516 that allows device 500 to communicate with other computing devices 518, such as over a network in a distributed computing environment, for example, an intranet or the Internet. Communication connection 516 is one example of communication media.

According to an aspect, program modules, such as the claim valuation engine 104, include routines, programs, components, data structures, and other types of structures that perform particular tasks or that implement particular abstract data types. Moreover, according to an aspect, features of the present disclosure are practiced with other computer system configurations, such as hand-held devices, multiprocessor systems, microprocessor-based or programmable user electronics, minicomputers, mainframe computers, and the like. According to an aspect, features of the present disclosure are practiced in distributed computing environments where tasks are performed by remote processing devices that are linked through a communications network. In a distributed computing environment, program modules are located in both local and remote memory storage devices.

Furthermore, according to an aspect, features of the present disclosure are practiced in an electrical circuit comprising discrete electronic elements, packaged or integrated electronic chips containing logic gates, a circuit utilizing a microprocessor, or on a single chip containing electronic elements or microprocessors. According to an aspect, features of the disclosure are practiced using other technologies capable of performing logical operations such as, for example, AND, OR, and NOT, including but not limited to mechanical, optical, fluidic, and quantum technologies. According to an aspect, features of the disclosure are practiced within a general purpose computer or in any other circuits or systems.

Aspects of the present disclosure, for example, are implemented as a computer process (method), a computing system, or as an article of manufacture, such as a computer program product or computer readable media. The computer program product may be a computer storage media readable by a computer system and encoding a computer program of instructions for executing a computer process. Accordingly, the aspects of the present disclosure may be embodied in hardware and/or in software (including firmware, resident software, micro-code, etc.). In other words, aspects of the present disclosure may take the form of a computer program product on a computer-usable or computer-readable storage medium having computer-usable or computer-readable program code embodied in the medium for use by or in connection with an instruction execution system.

Although aspects of the present disclosure have been described as being associated with data stored in memory and other storage mediums, data is also storable on or readable from other types of computer-readable media, such as secondary storage devices, like hard disks, floppy disks, or a CD-ROM, or other forms of RAM or ROM. The term computer-readable storage medium refers only to devices and articles of manufacture that store data and/or computer-executable instructions readable by a computing device. Computer-readable storage media do not include communications media.

According to an aspect, features of the present disclosure are utilized in various distributed computing environments where tasks are performed by remote processing devices that are linked through a communications network.

The description and illustration of one or more aspects provided in this application are intended to provide a complete thorough and complete disclosure the full scope of the subject matter to those skilled in the art and not intended to limit or restrict the scope of the invention as claimed in any way. The aspects, examples, and details provided in this application are considered sufficient to convey possession and enable those skilled in the art to practice the best mode of claimed invention. Descriptions of structures, resources, operations, and acts considered well-known to those skilled in the art may be brief or omitted to avoid obscuring lesser known or unique aspects of the subject matter of this application. The claimed invention should not be construed as being limited to any embodiment, example, or detail provided in this application unless expressly stated herein. Regardless of whether shown or described collectively or separately, the various features (both structural and methodological) are intended to be selectively included or omitted to produce an aspect with a particular set of features. Further, any or all of the functions and acts shown or described may be performed in any order or concurrently. Having been provided with the description and illustration of the present application, one skilled in the art may envision variations, modifications, and alternate embodiments falling within the spirit of the broader aspects of the general inventive concept embodied in this application that do not depart from the broader scope of the claimed invention.

We claim:

1. A system comprising:
an input module operable to:
   receive contract terms, rates, and criteria in association with a contract between a healthcare provider and a payer for valuing a claim;
   build the contract from the contract terms including a priority level for each contract term to create a valuation hierarchy for the contract terms, a category to describe each contract term, and a valuation type that corresponds to a type of calculation to perform to value each contract term, rates, and criteria to enable matching of one or more of the contract terms with one or more claim attributes of a claim;
   link the contract with the payer;
   store the contract in a contracts repository as an existing contract; and
   receive the claim comprising the one or more claim attributes;
a valuation table to include the one or more claim attributes, and contract terms of existing contracts and/or proposed contracts organized according to the valuation hierarchy;
a claim attribute extraction module operable to:
   access the claim;
   identify a payer responsible for payment of the claim;
   read the one or more claim attributes from the claim; and
   load the claim attributes into the valuation table;
a payer-contract mapping module coupled to the claim attribute extraction module operable to locate a contract linked to an identified payer;
a contract term extraction module coupled to the payer-contract mapping module operable to read the located contract and load contract terms associated with the identified payer in conjunction with one or more proposed contract terms of a proposed contract derived from the contract terms associated with the identified payer of the located contract into the valuation table according to the priority level of each contract term;
a simulation module coupled to the input module, the contract term extraction module, the claim attribute extraction module, and the valuation table, the simulation module to simulate valuation of the one or more proposed contract terms of the proposed contract in conjunction with one or more of the claim attributes to enable creation of another contract for the identified payer based on a valuation of one or more of the claim attributes with one or more of the contract terms associated with the identified payer of the located contract and the valuation of the one or more proposed contract terms of the proposed contract;

an attribute-term correlation module coupled to the valuation table operable to correlate claim attributes or groups of claim attributes with the contract terms included in the valuation table according to the priority level of each contract term, wherein the attribute-term correlation module operates to first correlate contract terms having a first priority value with the claim attributes included in the valuation table; and a valuation module coupled to the valuation table operable to:
for a correlation made by the attribute-term correlation module:
value the claim attributes or groups of claim attributes that correlate with the contract terms of the located contract according to the valuation hierarchy and a valuation type;
generate an expected reimbursement value for the claim according to the contract terms of the located contract;
compare an actual reimbursement for the claim to the expected reimbursement value for the claim to identify a payment variance; and
generate an expected reimbursement value for the claim according to the one or more proposed contract terms of the proposed contract and the valuation type; and a report module operable to generate a simulation report for one or more procedures associated with the claim that have a greater expected reimbursement value according to the contract terms of the located contract as compared to the expected reimbursement value for the claim according to the one or more proposed contract terms of the proposed contract.

2. The system of claim 1, the report output module further operable to:
generate a valuation report comprising an expected reimbursement value for the claim; and
post the valuation report to a host system.

3. The system of claim 2, wherein the valuation module is further operable to:

analyze a charge amount for each claim attribute or group of claim attributes and the value of each claim attribute or group of claim attributes; and
generate an allowance value for each claim attribute or group of claim attributes.

4. The system of claim 3, further comprising a remittance validation module operable to:
access remittance information associated with the claim, wherein remittance information comprises a remitted amount for each claim attribute or group of claim attributes;
analyze the remitted amount for each claim attribute or group of claim attributes and the value of each claim attribute or group of claim attributes; and
determine a variance between a remitted amount for each claim attribute or group of attributes and the value of each claim attribute or group of claim attributes.

5. The system of claim 4, wherein the report output module is further operable to:
generate a report comprising the generated allowance values;
generate a report comprising the determined variances between the remitted amount for each claim attribute or group of attributes and the value of each claim attribute or group of claim attributes; and
post the reports to the host system.

6. The system of claim 5, the simulation module further operable to:
receive a selection of an existing set of hierarchical contract terms and an input of a proposed set of hierarchical contract terms, wherein the hierarchical contract terms define criteria for valuing a claim;
receive a selection of a claim comprising one or more claim attributes; and
load the existing set of hierarchical contract terms, the proposed set of hierarchical contract terms, and claim attributes into the valuation table for valuation by the valuation module.

7. The system of claim 6, wherein the report output module is further operable to:
generate the simulation report comprising a value of each claim attribute or group of claim attributes based on the existing set of hierarchical contract terms and the proposed set of hierarchical contract terms; and
post the simulation report to the host system.

* * * * *